United States Patent [19]

Gapinski

[11] Patent Number: 4,996,230

[45] Date of Patent: Feb. 26, 1991

[54] LEUKOTRIENE ANTAGONISTS

[75] Inventor: D. Mark Gapinski, Lebanon, Ind.

[73] Assignee: Eli Lilly and Company, Indianapolis, Ind.

[21] Appl. No.: 481,413

[22] Filed: Feb. 16, 1990

[51] Int. Cl.$^5$ .................. A61K 31/35; C07D 311/80
[52] U.S. Cl. .................................. 514/454; 514/455; 549/393; 549/394
[58] Field of Search .............. 549/393, 394, 392; 514/454, 455

[56] References Cited

U.S. PATENT DOCUMENTS

| | | | |
|---|---|---|---|
| 4,166,819 | 9/1979 | Jones et al. | 548/253 |
| 4,337,353 | 6/1982 | Allais et al. | 562/460 |
| 5,242,121 | 12/1980 | Hawkins et al. | 71/93 |

FOREIGN PATENT DOCUMENTS

| | | |
|---|---|---|
| 150166 | 7/1985 | European Pat. Off. . |
| 276064 | 7/1988 | European Pat. Off. . |
| 278176 | 8/1988 | European Pat. Off. . |
| 1293626 | 10/1972 | United Kingdom . |
| 1543964 | 4/1979 | United Kingdom . |

Primary Examiner—Nicky Chan
Attorney, Agent, or Firm—Robert A. Conrad; Leroy Whitaker

[57] ABSTRACT

This invention provides tricyclic derivatives which are leukotriene B$_4$ antagonists, formulations of those derivatives, and a method of using those derivatives for the treatment of conditions characterized by an excessive release of leukotrienes.

14 Claims, No Drawings

LEUKOTRIENE ANTAGONISTS

BACKGROUND OF THE INVENTION

Research in the area of allergic reactions of the lung has provided evidence that arachidonic acid derivatives formed by the action of lipoxygenases are related to various disease states. Some of these arachidonic acid metabolites have been classified as members of a family of eicosatetraenoic acids termed leukotrienes. Three of these substances are currently thought to be major components of what has been previously called slow reacting substance of anaphylaxis (SRS-A).

Leukotriene $B_4$ ($LTB_4$) is a proinflammatory lipid which has been implicated in the pathogenesis of psoriasis, arthritis, chronic lung diseases, inflammatory bowel diseases, and other inflammatory states characterized by the infiltration and aggregation of polymorphonuclear leukocytes. Thus aggregated, the polymorphonuclear leukocytes liberate tissue-degrading enzymes and reactive chemicals causing the inflammation. Antagonism of $LTB_4$ should therefore provide a novel therapeutic approach to treatment of these conditions.

It is the object of this invention to provide novel chemical agents which are selective leukotriene antagonists that can be used therapeutically in the treatment of inflammation and allergic disorders such as asthma, where leukotrienes are thought to be causal mediators.

SUMMARY OF THE INVENTION

This invention provides compounds of the Formula I

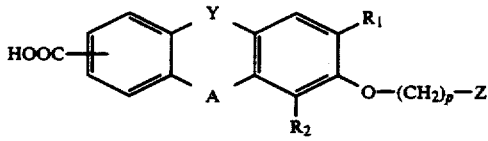

or a pharmaceutically acceptable base addition salt thereof, wherein

Y is —CO—, —C(=NOH)—, —CHOH—, —CH₂—, or —C(=CH₂)—;

A is a bond or —O—;

one of $R_1$ and $R_2$ is hydrogen and the other of $R_1$ and $R_2$ is —CH₂CH₂COOH;

p is 1–16; and

Z is —H or —G—Q where

G is a bond, —O—, —S(O)$_t$—, —NH—, —CH=CH—, or —C≡C—,

Q is phenyl or phenyl substituted with one or two substituents selected from the group consisting of halo, $C_1$–$C_3$ alkyl, $C_1$–$C_3$ alkoxy, acetyl, nitro, amino, trifluoromethyl, hydroxy, and —S(O)$_t$—($C_1$–$C_3$ alkyl), and each t is independently 0–2.

Further provided by this invention is a method for treating immediate hypersensitivity conditions such as inflammation or asthma comprising the administration of an effective amount of a compound of Formula I.

This invention also provides a pharmaceutical formulation which comprises as an active ingredient a compound of this invention as defined above associated with a pharmaceutically acceptable carrier therefor.

DETAILED DESCRIPTION OF THE PREFERRED EMBODIMENT

The present invention relates to new organic compounds that are useful in the treatment of immediate hypersensitivity reactions. A preferred group of compounds are the compounds of Formula Ia:

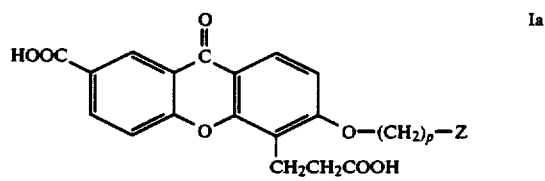

and pharmaceutically acceptable base addition salts thereof wherein p' is 4–12.

Preferred Z substituents include hydrogen, ortho- and para-substituted phenyl, especially 4-methoxyphenyl, and —CH=CH—(para-substituted phenyl).

The following definitions refer to the various terms used throughout this disclosure.

The term "$C_1$–$C_3$ alkyl" refers to the straight and branched aliphatic radicals of 1 to 3 carbon atoms such as methyl, ethyl, propyl, and isopropyl. The term "$C_1$–$C_3$ alkoxy" refers to methoxy, ethoxy, propoxy, and isopropoxy. The term "halo" refers to fluoro, chloro, bromo, and iodo.

This invention include the pharmaceutically acceptable base addition salts of the compounds of Formula I. Such salts include those derived from inorganic bases, such as ammonium and alkali and alkaline earth metal hydroxides, carbonates, bicarbonates, and the like, as well as salts derived from basic organic amines, such as aliphatic and aromatic amines, aliphatic diamines, hydroxy alkylamines, and the like. Such bases useful in preparing the salts of this invention thus include ammonium hydroxide, potassium carbonate, sodium bicarbonate, calcium hydroxide, methyl amine, diethyl amine, ethylene diamine, cyclohexylamine, ethanolamine, and the like. The potassium and sodium salt forms are particularly preferred.

It is recognized that when Y is —C(=NOH)— or —CHOH—, or when G is —CH=CH—, various stereoisomeric products may exist. This invention is not limited to any particular stereoisomer but includes all possible individual isomers and mixtures thereof.

The compounds of this invention may be prepared according to standard methods known in the art. For example, the xanthone derivatives of Formula I (I, A=O, Y=C=O) may be prepared according to Scheme I:

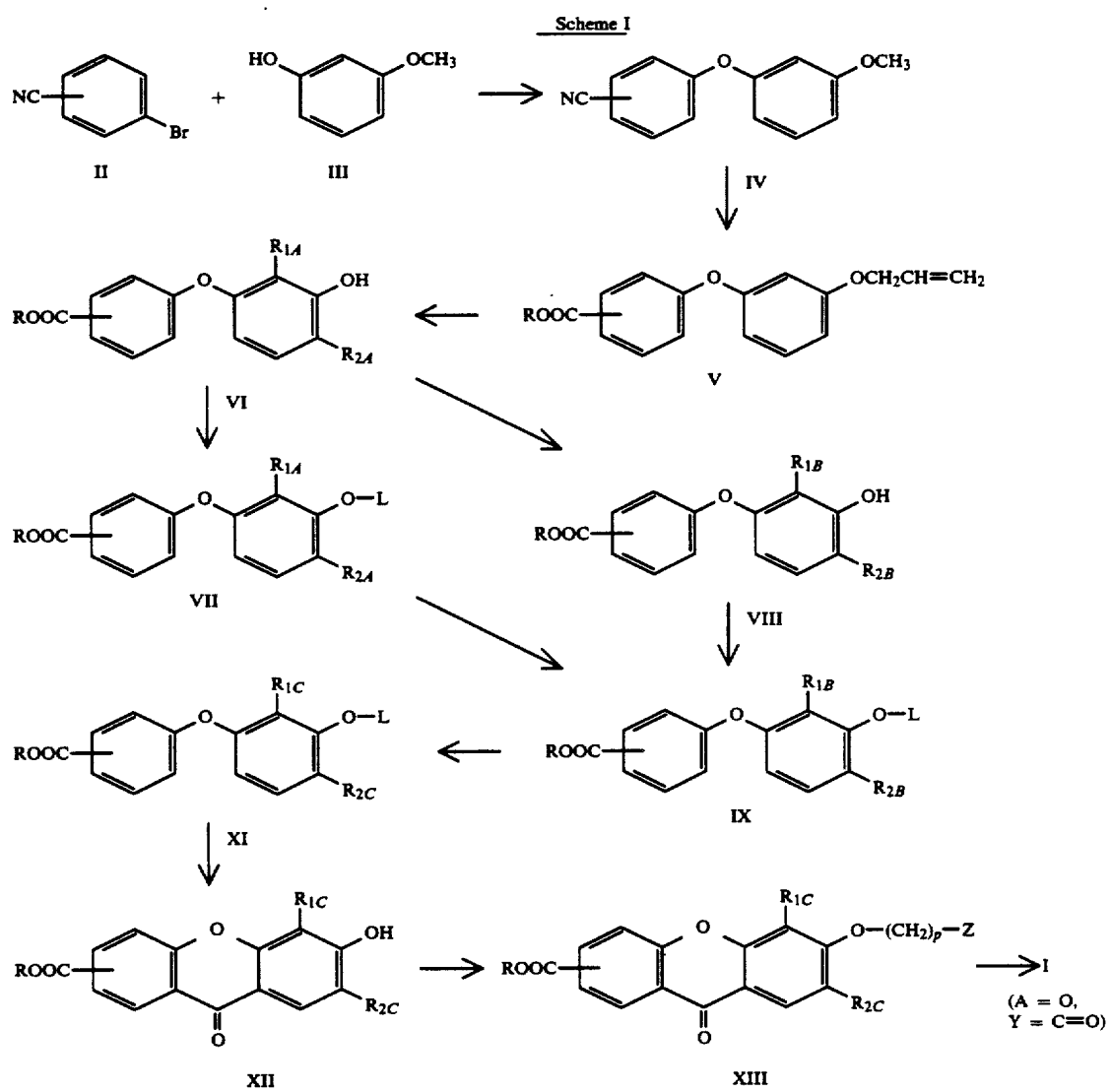

Scheme I wherein: R is $C_1$-$C_4$ alkyl or a similar group which provides an ester moiety which can be easily removed, L is a protecting group or $C_1$-$C_{10}$ alkyl one of $R_{1A}$ and $R_{2A}$ is allyl and the other is hydrogen, one of $R_{1B}$ and $R_{2B}$ is —$CH_2CH_2CH_2OH$ and the other is hydrogen, and one of $R_{1C}$ and $R_{2C}$ is —$CH_2CH_2COOR$ and the other is hydrogen.

According to Scheme I, a cyanophenyl bromide II is condensed with 3-methoxyphenol in the presence of powdered copper and a base such as potassium carbonate to provide the diaryl ether IV. This reaction is generally known as an Ullmann Reaction Intermediate IV is then converted into Intermediate V by the following steps. First, the nitrile is hydrolyzed to the corresponding carboxylic acid by standard means. Next, the methoxy functionality is deblocked by heating in molten pyridine hydrochloride to transform the methoxy group into the corresponding phenol. The carboxylic acid functionality is then converted into the corresponding ester. This transformation is accomplished by standard methods, such as heating the acid in the presence of an alkanol, such as methanol or ethanol, in which a mineral acid has been added. Finally, the phenol is alkylated with allyl bromide or chloride in the presence of a base such as potassium carbonate, in a nonreactive solvent, such as methyl ethyl ketone, to provide the allyloxy Intermediate V. This alkylation procedure is catalyzed by small amounts of added sodium or potassium iodide as will be appreciated by one skilled in this art.

Intermediate V is then heated at approximately 200° C. to prepare intermediates VI. This transformation is the classic Claisen rearrangement wherein the allyl functionality migrates to either of the positions ortho to the resulting phenol. The allyl derivative VI can then be oxidized to the corresponding alcohol VIII employing 9-BBN (9-borabicyclo[3.3.1]nonane) in a nonreactive solvent such as tetrahydrofuran. The phenol functionality of Intermediate VIII can the be alkylated with a protecting group or $C_1$-$C_{10}$ alkyl functionality, to prepare Intermediates IX. This alkylation is essentially the same as the introduction of the allyl functionality onto the phenol described above. Alternatively, intermediate VI can first be alkylated to provide the phenol-protected Intermediate VII which is then oxidized to prepare the alcohol IX.

The propanol derivative IX is then transformed to the corresponding propionic acid XI using a suitable oxidizing reagent. A preferred method of accomplishing this transformation is the use of Jones reagent (chromic anhydride and dilute sulfuric acid). The resulting propanoic acid derivative is then transformed into its corresponding ester by treatment with a suitable alkanol and mineral acid to provide Intermediate XI. This diaryl ether XI is then converted into the corresponding xanthone under Friedel-Crafts acylation conditions. In particular, Intermediate XI is treated with a Lewis acid, vide the diester derivative XIII. Hydrolysis of the esters of Formula XIII may be accomplished by any of a variety of acidic or basic conditions, preferable under aqueous conditions. The preferred method involves the use of potassium hydroxide in a mixture of water with either methanol or ethanol. Under these preferred conditions, hydrolysis is usually complete in about 1 hour at 20°–30° C. The resulting product is a xanthone derivative of Formula I.

Processes for preparing the preferred xanthones of Formula Ia are described in Scheme II:

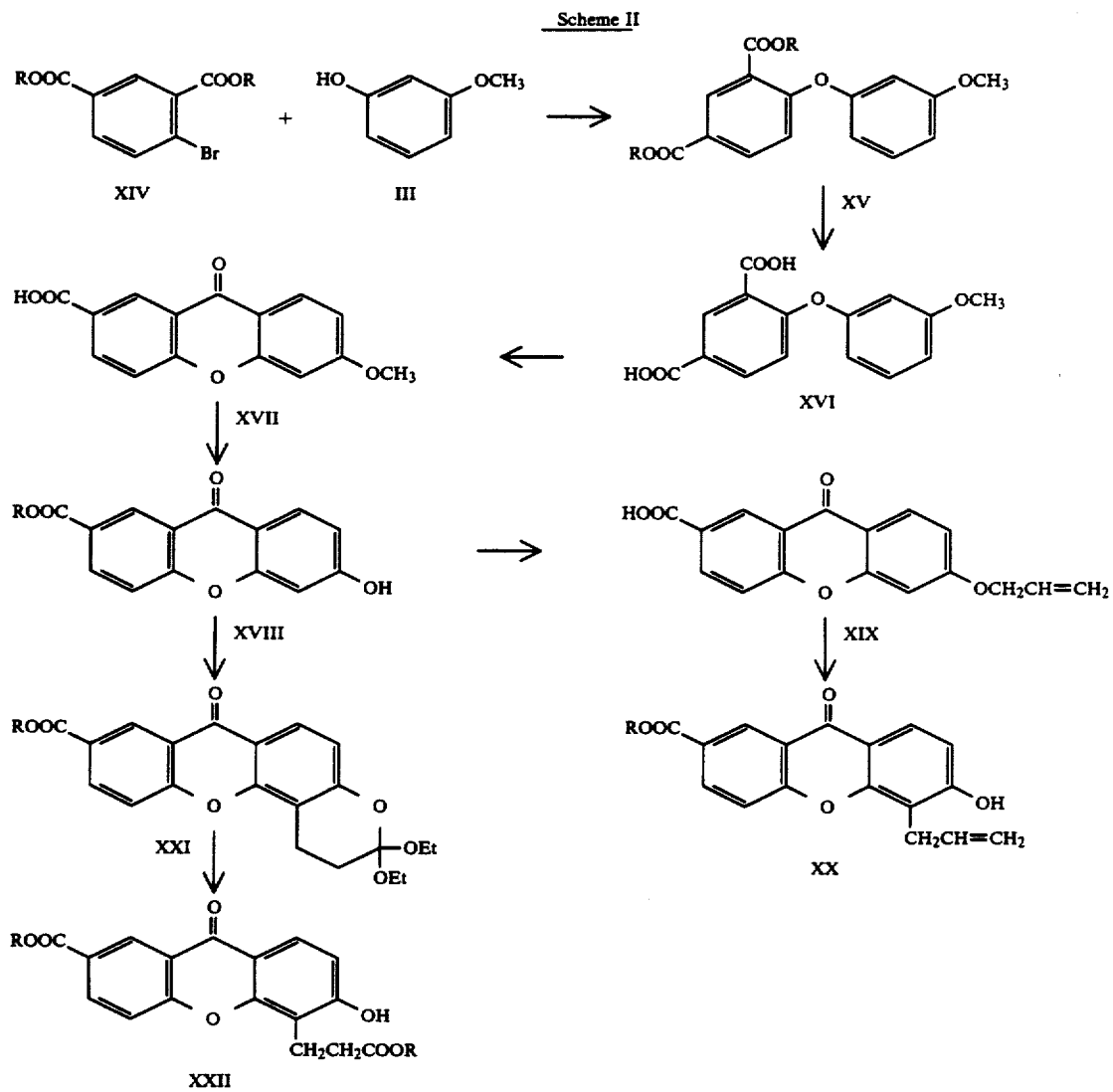

Scheme II such as aluminum chloride, and oxalyl chloride in the presence of a nonreactive solvent, preferably dichloromethane. The reaction is best carried out at temperatures from about 0° to about 25° C. and is generally complete within 2–4 hours. This reaction is usually effective at removing the phenol protecting or alkyl group L to regenerate the phenol functionality. Phenol XII can then be alkylated with the appropriate alkyl halide Z—(CH$_2$)$_p$—X, wherein X is a good leaving group such as iodo, bromo, chloro, or mesyl, in the presence of a base, such as sodium hydride or potassium carbonate, and preferably in a nonreactive solvent such a dimethylformamide or methyl ethyl ketone, to pro- According to Scheme II, the diester of Formula XIV is condensed with 3-methoxyphenol under Ullmann reaction conditions as described above in Scheme I to provide the bisaryl ether XV. Hydrolysis of both ester groups provides the diacid of Formula XVI which is then ring closed to provide the xanthone of Formula XVII. The cyclization of Intermediate XVI is accomplished by the use of a Lewis acid, and in particular phosphorous pentoxide, in a strongly acidic solvent, such as methanesulfonic acid. Such a reaction is virtually instantaneous when carried out at ambient temperature. The resulting methoxy-substituted xanthone XVII is then treated with molten pyridine hydrochloride as described in Scheme I above to provide the phenol XVIII. The phenol can then be alkylated with an allyl halide to provide Intermediate XIX and heated to provide the allyl Intermediate XX (Claisen rearrangement). This latter transformation provides only the preferred allyl-substituted xanthone XX which can then be oxidized, alkylated, and deesterified as described above in Scheme I.

Alternatively, Intermediate XVIII can be treated with a trialkyl orthoacrylate in the presence of an acid such as trimethylacetic acid in a nonreactive solvent such as toluene. This reaction in the preparation of the orthoacrylate intermediate is described by Stetter, *Synthesis*, 207 (1973) and is useful for preparing tetracyclic cyclic ketal derivative XXI which, upon treatment with dilute mineral acid in an nonreactive organic solvent, such as ethyl acetate, converts the "ortho lactone" of Formula XXI into the desired ethyl propionate derivative XXII which can be alkylated and deesterified in the same manner as described in Scheme I above to provide the preferred xanthone generally by Rapaport et al., *J. Org. Chem.*, 47, 346 (1982).

The fluorenone derivatives of Formula I (I, A=a bond, Y=—CO—) are prepared in the following manner.

give the amide (XXIII, T=—NHC(CH₃)₂CH₂OH). As is well known in the art, treatment of this type of amide derivative with neat thionyl chloride at room temperature for about an hour results in the cyclized oxazoline intermediate XXIV. In the same way, the appropriate bromobenzoic acid XXV (T=—OH) can be transformed into oxazoline intermediate XXVI. The latter intermediate is then treated with magnesium in a solvent such as tetrahydrofuran to prepare the Grignard derivative of XXVI which is allowed to react with XXIV in an inert solvent such as tetrahydrofuran to give the biphenyl intermediate XXVII. This doubly protected bisoxazoline derivative is then hydrolyzed, such as in the presence of refluxing hydrochloric acid, to give the biphenyldiacid XXVIII. Ring closure of this latter intermediate to fluorenone intermediate XXIX can then be effected by any of a number of dehydrating reagents, such as a mixture of phosphorous pentoxide and methanesulfonic acid. This fluorenone nucleus can then be functionalized and transformed to the corresponding compounds of this invention in the same manner as described above for intermediates IV and XVII.

From the above methods of preparing the ketone compounds of this invention (Formula I, Y is —CO—), compounds having various other Y functionalities may be prepared For example, the ketone group can be reduced to the corresponding carbinol (I, Y is

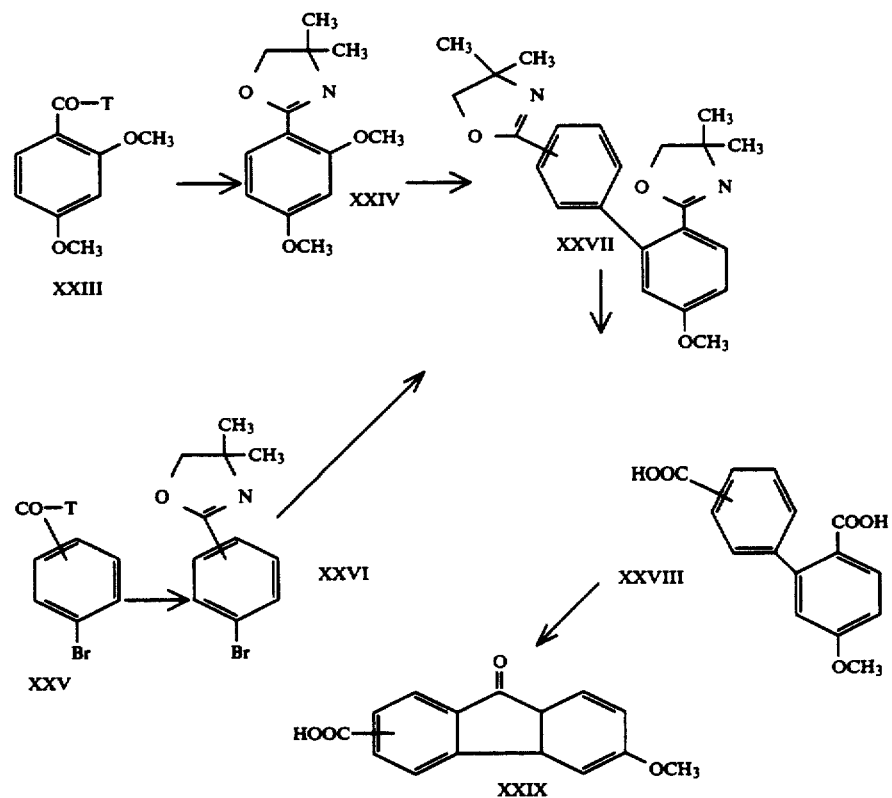

where T is —OH, —Cl, or —NHC(CH₃)₂CH₂OH as described below.

According to the scheme outlined above, 2,4-dimethoxybenzoic acid (XXIII, T=—OH) is converted into the corresponding acid halide, particularly the acid chloride (XXIII, T=—Cl), by standard methods, then allowed to react, preferably in an inert solvent such as dichloromethane, with 2-amino-2-methyl-1-propanol to —CHOH—). The most convenient method for effecting this transformation is treating the ketone with sodium borohydride in a solvent such as ethanol. To reduce the carbinol completely to the diphenylmethane derivative (I, Y is —CH₂—), reduction of the carbinol with hydrogen gas over a catalyst, such as palladium on carbon, is preferred. Standard reaction conditions in non-reactive solvents may be employed; acetic acid is a preferred solvent for this transformation. For either of these reduction steps, it is preferred that the ester intermediate be employed as compared with the carboxylic acid. After reduction, hydrolysis of the ester to the acid may be effected in the normal way.

Similarly, the ketone may be transformed into the oxime (Formula I, Y is —C(=NOH)—) upon treatment with hydroxylamine. The hydrochloride of hydroxylamine is usually employed although a non-reactive acid-scavenging solvent, such as pyridine, is best employed Once again, it is preferred that this transformation be performed on the ester form of the compound with hydrolysis to the carboxylic acid by standard methods to follow.

The ethylene analogs of this invention (I, Y is —C(=CH$_2$)—) may also be prepared from the benzophenones according to known methods. This transformation involves a Wittig reaction which is performed on a ketone intermediate before the introduction of any other reactive group, such as a carboxylic acid. Typically, a slight molar excess of an ylid precursor, such as methyl triphenylphosphine bromide, and a strong organic base, such as N-butyllithium, in a non-reactive solvent such as tetrahydrofuran, are employed After the introduction of the ethene functionality, other derivatizations as previously described may be performed.

The thio derivatives and intermediates of this invention (t is 0) may be transformed into the corresponding sulfoxide (t is 1) compounds upon treatment with a mild oxidizing agent, such as hydrogen peroxide in methanol, meta-chloroperoxybenzoic acid (MCPBA) in methylene chloride at 0° C., or an alkali metal periodate in aqueous alcohol The corresponding sulfones (t is 2) in aqueous alcohol The corresponding sulfones (t is 2) are prepared from the thio or sulfoxide compounds on treatment with a strong oxidizing agent such as hydrogen peroxide in acetic acid or m-chloroperbenzoic acid in methylene chloride at 20°-30° C. In addition, various compounds of Formula I can be prepared from other compounds, precursors, or intermediates of Formula I by standard methods such as hydrolysis, esterification, alkylation, oxidation, reduction, and the like, as are well known to those skilled in the art.

Intermediate compounds II, III, and XIV, and any other necessary reagents, are either commercially available, known in the literature, or can be prepared according to methods known in the art.

The following examples further illustrate the preparation of the intermediates and compounds of this invention. The examples are illustrative only and are not intended to limit the scope of the invention. Where structures were confirmed by infra-red, proton nuclear magnetic resonance, or mass spectral analysis, the compound is so designated by "IR", "NMR", or "MS", respectively.

EXAMPLE 1

5-Carboxy-3-(decyloxy)-9-oxo-9H-xanthene-2-propanoic acid

A. Preparation of 2-(3-methoxyphenoxy)benzonitrile

A mixture of 100 g of 2-tromobenzonitrile, 68.1 g of 3-methoxyphenol, 35 g of powdered copper, and 75.8 g of potassium carbonate was heated at reflux in 3 liters of pyridine for 6 days. The reaction mixture was filtered hot, cooled to room temperature, and concentrated in vacuo. To the residue were slowly added 1.5 liters of concentrated hydrochloric acid. Ethyl acetate and water were added and the layers were separated. The organic layer was washed several times with water, dried over sodium sulfate, and concentrated in vacuo. The residue was purified in several portions by high pressure liquid chromatography over silica gel eluting with a hexane to 10% ethyl acetate in hexane gradient providing 53.4 g of the desired subtitled intermediate as an oil which crystallized upon standing.

Analysis for $C_{14}H_{11}NO_2$: Calc.: C, 74.65; H, 4.92; N, 6.22; Found: C, 74.95; H, 5.17; N, 6.24.

B. Preparation of 2-(3-methoxyphenoxy)benzoic acid

A mixture of 48.2 g of the intermediate from Example 1A above and 20 g of potasium hydroxide in a mixture of ethanol and water was heated at reflux overnight. After cooling to room temperature, the solution was concentrated in vacuo. Ethyl acetate and water were added, the layers were separated, and the separated aqueous layer was acidified. The acidified aqueous layer was extracted with ethyl acetate, and the organic layer dried and concentrated in vacuo. The residue was crystallized from ethyl acetate/hexane providing of 18.81 g of the desired subtitle intermediate, m.p. 129°-131° C.

Analysis for $C_{14}H_{12}O_4$: Calc. C, 68.85; H, 4.95; Found: C, 68.57; H, 4.02.

C. Preparation of 2-(2-hydroxyphenoxy)benzoic acid

Fifteen grams of 2-(2-methoxyphenoxy)benzoic acid were heated at 180°-185° C. together with 150 g of pyridine hydrochloride for 3 hours. After cooling to room temperature, water was added and the mixture was stirred overnight at room temperature. The reaction was filtered and the water extracted several times with ethyl acetate. The combined ethyl acetate layers were dried and concentrated in vacuo. The crystallization of the residue from ethyl acetate/hexane provided 6.88 g of the desired subtitled intermediate, m.p. 147°-149° C.

Analysis for $C_{13}H_{10}O_4$: Calc.: C, 67.82; H, 4.38; Found: C, 67.55; H, 4.59.

D. Preparation of 2-(3-hydroxyphenoxy)benzoic acid ethyl ester

A solution of 17.8 g of 2-(3-hydroxyphenoxy)benzoic acid in 250 ml of ethanol and 1 ml of sulfuric acid was heated at reflux for two days. After cooling, the mixture was concentrated in vacuo. The residue was partitioned between ethyl acetate and water. The organic layer was dried and concentrated in vacuo. The resulting residue was purified by high pressure liquid chromatography eluting with a 0-30% ethyl acetate in hexane gradient. The appropriate fractions were combined and concentrated in vacuo to provide 16.78 g of the desired subtitled intermediate as an oil.

Analysis for $C_{15}H_{14}O_4$: Calc.: C, 69.76; H, 5.46; Found: C, 69.77; H, 5.68.

E. Preparation of 2-[3-(2-propenyloxy)phenoxy]benzoic acid ethyl ester

A mixture of 16.27 g of the intermediate from Example 1D above, 7.56 g of allyl bromide, 8.7 g of potassium carbonate, 500 mg of potassium iodide, and 500 ml of methyl ethyl ketone were heated at reflux for 4 days. After cooling to room temperature and filtration, the filtrate was washed with water, dried, and concentrated in vacuo providing 17.6 g of the desired subtitled intermediate as an oil which was used without further purification.

Analysis for $C_{18}H_{18}O_4$: Calc.: C, 72.47; H, 6.08; Found: C, 72.61; H, 6.10.

F. Preparation of 2-[3-hydroxy-2-(propenyl)phenoxy]benzoic acid ethyl ester and 2-[3-hydroxy-4-(2-propenyl)phenoxy]benzoic acid ethyl ester The 17.6 g of intermediate from Example 1E above were heated at 200° C. for 3 hours. After cooling to room temperature, the residue was purified by high pressure liquid chromatography over silica gel eluting with a 0–10% ethyl acetate in hexane gradient. A combination of the appropriate fractions and concentration in vacuo provided 12.5 g of a mixture of the isomeric title intermediates which were used in the subsequent reaction without separation.

Analysis for $C_{18}H_{18}O_4$: Calc.: C, 72.47; H, 6.08; Found: C, 72.23; H, 6.11.

G. Preparation of 2-[3-hydroxy-4-(3-hydroxypropyl)phenoxy]benzoic acid ethyl ester and 2-[3-hydroxy-2-(3-hydroxypropyl)phenoxy]benzoic acid ethyl ester In the mixture from Example 1F above (6.86 g) was dissolved in 200 ml of dry tetrahydrofuran. To this mixture were added 70 ml of a 0.5M solution of 9-BBN in tetrahydrofuran. The mixture was stirred overnight at room temperature at which time a 10 ml of 0.5M 9-BBN were added. After stirring an additional hour, sodium acetate and hydrogen peroxide were added. After stirring an additional hour, the layers were separated and the organic layer was dried and concentrated in vacuo. The residue was purified by high pressure liquid chromatography over silica gel eluting with a 0–50% ethyl acetate in hexane gradient. The appropriate fractions were combined and concentrated in vacuo to provide 1.93 g of the 2-(3-hydroxypropyl)isomer and 2.86 g of the 4-(3-hydroxypropyl)isomer of the title compounds. Both materials were oils.

2-[3-Hydroxy-2-(3-hydroxypropyl)phenoxy]benzoic acid ethyl ester.

Analysis for $C_{18}H_{20}O_5$: Calc.: C. 68.35; H, 6.37; Found: C, 68.13; H, 6.62.

2-[3-Hydroxy-4-(3-hydroxypropyl)phenoxy]benzoic acid ethyl ester.

Analysis for $C_{18}H_{20}O_5$: Calc.: C, 68.34; H, 6.37; Found: C, 68.35; H, 6.39.

H. Preparation of 2-[3-(decyloxy)-4-(3-hydroxypropyl)phenoxy]benzoic acid ethyl ester A mixture of 600 mg of 2-[3-hydroxy-4-(3-hydroxypropyl)phenoxy]benzoic acid ethyl ester, 0.4 ml of decyl iodide, and 0.26 g of potassium carbonate in 50 ml of methyl ethyl ketone was stirred at reflux overnight. After cooling to room temperature, the mixture was filtered and the filtrate concentrated in vacuo. Purification of the residue by column chromatography over silica gel eluting with 20% ethyl acetate in hexane provided 510 mg of the desired subtitled intermediate as an oil, MS, IR, NMR.

I. Preparation of 2-(decyloxy)-4-[2-(ethoxycarbonyl)phenoxy]benzenepropanoic acid ethyl ester To a solution of 490 mg of 2-[3-(decyloxy)-4-(3-hydroxypropyl)phenoxy]benzoic acid ethyl ester in ether were added 1 ml of Jones reagent (chromic acid solution). After stirring for 1 hour, additional ether was added and the solution washed with a sodium bisulfite solution. The organic layer was dried and concentrated in vacuo. To the residue were added ethanol and a few drops of sulfuric acid. The mixture was refluxed overnight, cooled to room temperature, and concentrated in vacuo. Ethyl acetate was added and the organic solution washed with water. The organic layer was dried, concentrated in vacuo, and the residue purified by column chromatography eluting with 5% ethyl acetate in hexane. Combination concentration of the appropriate fractions yielded 110 mg of the desired subtitled intermediate as an oil. MS, IR, NMR.

J. Preparation of 5-(ethoxycarbonyl)-3-hydroxy-9-oxo-9H-xanthene-2-propanoic acid To a solution of 0.7 g of 2-(decyloxy)-4-[2-(ethoxycarbonyl)phenoxy]benzenepropanoic acid ethyl ester in methylene chloride at room temperature were added 0.187 g of aluminum chloride followed by 0.122 ml of oxalyl chloride. After stirring for approximately 1 hour, the mixture was poured into a combination of ice and hydrochloric acid. After stirring for approximately 1 hour, the layers were separated and the organic layer was dried and concentrated in vacuo. The material was used without further purification in the subsequent reaction.

K. Preparation of 5-ethoxycarbonyl-3-(decyloxy)-9-oxo-9H-xanthene-2-propanoic acid ethyl ester The phenol from Example 1J above was treated with 0.23 ml of decyl iodide and 0.147 g of potassium carbonate in 50 ml of methyl ethyl ketone at reflux overnight. After cooling to room temperature, the material was concentrated in vacuo. The residue was purified by column chromatography over silica gel eluting with 10% ethyl acetate in hexane. The desired fractions were combined and concentrated to provide 141 mg of the desired subtitle intermediate, m.p. 61°–63° C.

Analysis for $C_{13}H_{40}O_7$: Calc.: C, 70.97; H, 7.69; Found: C, 71.28; H, 7.81.

L. Preparation of 5-carboxy-3-(decyloxy)-9-oxo-9H-xanthene-2-propanoic acid

The diester intermediate from Example 1K above (130 mg) was stirred with ethanol/water and potassium hydroxide for 2 hours. The mixture was concentrated in vacuo and ethyl acetate and water were added. The layers were separated and the aqueous layer was acidified. The desired product precipitated from the acid solution and was recovered by filtration. Crystallization from ethyl acetate/hexane provided 60 mg of the desired title product, m.p. 180°–182° C.

Analysis for $C_{27}H_{32}O_7$: Calc.: C, 69.21; H, 6.88; Found: C, 69.43; H, 6.92.

EXAMPLE 2

5-Carboxy-3-(decyloxy)-9-oxo-9H-xanthene-4-propanoic acid

A. Preparation of 2-[3-decyloxy-2-(3-hydroxypropyl)phenoxy]benzoic acid ethyl ester The subtitle intermediate was prepared in 84.1% yield from 2-[3-hydroxy-2-(3-hydroxypropyl)phenoxy]benzoic acid ethyl ester according to the procedure of Example 1H. IR, MS, NMR.

B. Preparation of 2-(decyloxy)-6-[2-(ethoxycarbonyl)phenoxy]benzene-propanoic acid ethyl ester The title product was prepared in 23.6% yield from the corresponding hydroxypropyl intermediate following the procedure of Example 1I. The intermediate was an oil.

Analysis for $C_{30}H_{42}O_6$: Calc.: C, 72.27; H, 8.49; Found: C, 72.50; H, 8.38.

C. Preparation of 5-(ethoxycarbonyl)-3-hydroxy-9-oxo-9H-xanthene-4-propanoic acid ethyl ester The title product was prepared from 1.12 g of the intermediate from Example 2B above following the procedure of Example 1J. The product was used in the following reaction without further purification.

D. Preparation of 5-(ethoxycarbonyl)-3-decyloxy-9-oxo-9H-xanthene-4-propanoic acid ethyl ester The subtitle intermediate was prepared in overall yield from the phenol intermediate of Example 2C above employing the procedure of Example 1K, m.p. 69°-70° C.

Analysis for $C_{31}H_{40}O_7$: Calc.: C, 70.97; H, 7.69; Found: C, 70.93; H, 7.64.

E. Preparation of 5-carboxy-3-(decyloxy)-9-oxo-9H-xanthene-4-propanoic acid The desired title product was prepared in yield from the diester intermediate of Example 2D above following the procedure of Example 1L, m.p. >210° C.

Analysis for $C_{27}H_{32}O_7$: Calc.: C, 69.21; H, 6.88; Found: C, 69.02; H, 6.89.

EXAMPLE 3

7-Carboxy-3-decyloxy-9-oxo-9H-xanthene-2-propanoic acid

A. Preparation of 4-[3-(2-propenyloxy)phenoxy]benzoic acid ethyl ester

The subtitle intermediate was prepared in yield from 4-(3-hydroxyphenoxy)benzoic acid ethyl ester according to the procedure of Example 1E. The desired product was an oil.

Analysis for $C_{18}H_{18}O_4$: Calc.: C, 72.47; H, 6.08; Found: C, 72.43; H, 6.27.

B. Preparation of 4-[3-hydroxy-4-(2-propenyl)phenoxy]benzoic acid ethyl ester and 4-[3-hydroxy-2-(2-propenyl)phenoxy]benzoic acid ethyl ester Following the general procedure of Example 1F above, 21.2 g of the propenyloxy intermediate from Example 3A above was heated at 180° C. for approximately hours to provide 8.01 g of the 4-propenyl isomer and 4.87 g of the 2-propenyl isomer.

4-[3-Hydroxy-4-(2-propenyl)phenoxy]benzoic acid ethyl ester, oil.

Analysis for $C_{18}H_{18}O_4$: Calc.: C, 72.47; H, 6.08; Found C, 72.54; H, 6.26.

4-[3-Hydroxy-2-(2-propenyl)phenoxy]benzoic acid ethyl ester, m.p. 85°-88° C.

Analysis for $C_{18}H_{18}O_4$: Calc.: C, 72.47; H, 6.08; Found: C, 72.69; H, 6.22.

C. Preparation of 4-[3-(decyloxy)-4-(2-propenyl)phenoxy]benzoic acid ethyl ester Following the general procedure of Example 1H above, 7.11 g of 4-[3-hydroxy-4-(2-propenyl)phenoxy]benzoic acid ethyl ester was allowed to react with 6.38 g of decyl iodide in the presence of 3.3 g of potassium carbonate to provide 5.02 g of the desired subtitle intermediate as an oil.

Analysis for $C_{28}H_{38}O_4$: Calc.: C, 76.68; H, 8.73; Found: C, 76.80; H, 8.77.

D. Preparation of 4-[3-(decyloxy)-4-(3-hydroxypropyl)phenoxy]benzoic acid ethyl ester Following the procedure of Example 1G, 5.74 g of 4-[3-(decyloxy)-4-(2-propenyl)phenoxy]benzoic acid was oxidized to the title hydroxypropyl intermediate which was recovered as an oil. MS, IR, NMR.

Analysis for $C_{28}H_{40}O_5$: Calc.: C, 73.65; H, 8.83; Found: C, 70.96; H, 9.51.

E. Preparation of 2-(decyloxy)-4-[4-(ethoxycarbonyl)phenoxy]benzene-propanoic acid ethyl ester Following the procedure of Example 1I above, 3.01 g of the intermediate from Example 3D was oxidized and converted to the corresponding ethyl ester to provide 750 mg of the desired subtitle intermediate as an oil. MS, IR, NMR.

Analysis for $C_{30}H_{42}O_6$: Calc.: C, 72.26; H, 8.49; Found: C, 71.66; H, 8.20.

F. Preparation of 7-(ethoxycarbonyl)-3-hydroxy-9-oxo-9H-xanthene-2-propanoic acid ethyl ester Following the procedure of Example 1J above, 390 mg of the diester from Example 3E above was transformed into 200 mg of the subtitle xanthone. The product was characterized by MS, IR, NMR.

G. Preparation of 7-(ethoxycarbonyl)-3-(decyloxy)-9-oxo-9H-xanthene-2-propanoic acid ethyl ester The subtitle intermediate was prepared in 50.4% yield from the phenol of Example 3G above. MS, IR, NMR.

H. Preparation of 7-carboxy-3-(decyloxy)-9-oxo-9H-xanthene-2-propanoic acid

The title product was prepared from 130 mg of the corresponding diester following the procedure of Example 1L. The resulting 94.8 mg of product at a melting point greater than 210° C.

Analysis for $C_{27}H_{32}O_7$: Calc.: C, 69.21; H, 6.88; Found: C, 69.05; H, 6.97.

EXAMPLE 4

7-Carboxy-3-(decyloxy)-9-oxo-9H-xanthene-4-propanoic acid

A. Preparation of 4-[3-(decyloxy)-2-(3-hydroxypropyl)phenoxy]benzoic acid ethyl ester The subtitle product was prepared in 67.1% yield following the procedure of Example 1G from 4-[3-hydroxy-2-(3-hydroxypropyl)phenoxy]benzoic acid ethyl ester.

Analysis for $C_{28}H_{40}O_5$: Calc.: C, 73.65; H, 8.83; Found: C, 73.56; H, 8.61.

B. Preparation of 2-(decyloxy)-6-[4-(ethoxycarbonyl)phenoxy]benzenepropanoic acid ethyl ester Following the general procedure of Example 1I above, the subtitle intermediate was prepared in 61.9% yield from the corresponding hydroxypropyl intermediate. MS, IR, NMR.

C. Preparation of 7-(ethoxycarbonyl)-3-hydroxy-9-oxo-9H-xanthene-4-propanoic acid ethyl ester Following the procedure of Example 1J, 66 mg of the desired subtitle intermediate were prepared from mg of the corresponding bisaryl ether precursor. MS, IR, NMR.

D. Preparation of 7-(ethoxycarbonyl)-3-decyloxy-9-oxo-9H-xanthene-4-propanoic acid ethyl ester The subtitle intermediate was prepared in yield from the phenol precursor according to the procedure of Example 1K. The intermediate was an oil. IR, MS, NMR.

E. Preparation of 7-carboxy-3-decyloxy-9-oxo-9H-xanthene-4-propanoic acid

Following the procedure of Example 1L, 119 mg of the desired title product was prepared from 160 mg of the corresponding diester, m.p. >210° C.

Analysis for $C_{27}H_{32}O_7$: Calc.: C, 69.21; H, 6.88; Found: C, 69.41; H, 6.71.

EXAMPLE 5

5-Allyl-6-hydroxy-9-oxo-9H-xanthene-2-carboxylic acid ethyl ester

A. Preparation of 4-(3-methoxyphenoxy)-1,3-benzenedicarboxylic acid diethyl ester Following the general procedure of Example 1A, 3.49 g of 4-bromo-1,3-benzenedicarboxylic acid diethyl ester and 1.43 g of 3-methoxyphenol were allowed to react in the presence of powdered copper metal to provide 1.66 g of the desired subtitle intermediate as an oil.

Analysis for $C_{19}H_{20}O_6$: Calc.: C, 66.27; H, 5.85; Found: C, 66.50; H, 6.03.

B. Preparation of 4-(3-methoxyphenoxy)-1,3-benzenedicarboxylic acid

The title product was prepared in 79.6% yield from the corresponding diester according to the general procedure of Example 1B, m.p. 232°-234° C.

Analysis for $C_{15}H_{12}O_6$: Calc.: C, 62.50; H, 4.20; Found: C, 62.71; H, 4.32.

C. Preparation of 6-methoxy-9-oxo-9H-xanthene-2-carboxylic acid

To a solution of 17.25 g of phosphorous pentoxide in 17 ml of methanesulfonic acid under a nitrogen atmosphere were dissolved 15.4 g of the bis aryl ether prepared in Example 5B above. The mixture was stirred at room temperature overnight and then poured into ice. After stirring one hour, the aqueous layer was extracted with ethyl acetate. The organic Crystallization from methanol provided 12.7 g of the desired subtitle intermediate, m.p. >250° C.

Analysis for $C_{15}H_{40}O_5$: Calc.: C, 66.67; H, 3.93; Found: C, 66.47; H, 3.93.

D. Preparation of 6-hydroxy-9-oxo-9H-xanthene-2-carboxylic acid

Following the general procedure of Example 1C, the 12.7 g of methoxy intermediate from Example 5C was heated at 190° C. in the presence of pyridine hydrochloride to provide 10.6 g of the desired title phenol. NMR.

E. Preparation of 6-hydroxy-9-oxo-9H-xanthene-2-carboxylic acid ethyl ester

Following the procedure of Example 1D, the 10.6 g of phenol intermediate from Example 5D above was refluxed in the presence of ethanol/water and sulfuric acid for 13 days. Workup of the reaction in the same way provided 8.16 g of the desired subtitle ester, m.p. 250° C.

Analysis for $C_{16}H_{12}O_5$: Calc.: C, 67.60; H, 4.26; Found: C, 67.51; H, 4.32.

F. Preparation of 9-oxo-6-(2-propenyloxy)-9H-xanthene-2-carboxylic acid ethyl ester To a solution of 7.84 g of the intermediate from Example 5E above in 200 ml of dimethylformamide were added 1.1 g of a 60% dispersion in mineral oil of sodium hydride. After stirring for 1 hour, 2.38 ml of allyl bromide were added and the reaction stirred at 65° C. overnight. After cooling to room temperature, ethyl acetate was added and the solution washed with a saturated sodium chloride solution. The organic layer was dried and concentrated in vacuo. Purification by high pressure liquid chromatography over silica gel eluting with a 5-30% ethyl acetate in hexane gradient provided 5.4 g of the desired title intermediate m.p 133°-135° C.

Analysis for $C_{19}H_{16}O_5$: Calc.: C, 70.36; H, 4.97; Found: C, 70.62; H, 5.02.

G. Preparation of 5-allyl-6-hydroxy-9-oxo-9H-xanthene-2-carboxylic acid ethyl ester The 5.4 g of intermediate from Example 5F was heated at 190° C. according to the procedure of Example 1F. A portion of the material was purified by trituration with hot ethyl acetate providing the title compound, m.p. 126°–129° C.

Analysis for $C_{19}H_{16}O_5$: Calc.: C, 70.36; H, 4.97; Found: C, 70.31; H, 5.02.

This intermediate can then be alkylated, oxidized, and hydrolyzed to provide the preferred compounds of Formula Ia.

EXAMPLE 6

7-Carboxy-3-{[6-(4-methoxyphenyl)-5-hexenyl]oxy}-9-oxo-9H-xanthene-4-propanoic acid

A. Preparation of 3,3-diethoxy-2,3-dihydro-7-oxo-1H,7H-pyrano[2,3-c]xanthene-9-carboxylic acid A solution of 1.0 g of 6-hydroxy-9-oxo-9H-xanthene-2-carboxylic acid methyl ester and 1.37 g of triethylorthoacrylate (prepared according to the procedure of Stetter, *Synthesis*, 207 (1973)) in 25 ml of toluene was heated at reflux overnight. After cooling to room temperature, the desired product crystallized out of solution and was recovered by filtration. Recrystallization from ethyl acetate/hexane provided 1.1 g of the desire subtitle intermediate, m.p. 191°–193° C.

Analysis for $C_{22}H_{22}O_7$: Calc.: C, 66.32; H, 5.57; Found: C, 66.54; H, 5.72.

B. Preparation of 7-methoxycarbonyl-3-hydroxy-9-oxo-9H-xanthene-4-propanoic acid ethyl ester The "ortho lactone" from Example 6A above was dissolved in 20 ml of ethyl acetate. Five milliliters of a 10% hydrochloric acid solution were added. After 2 hours, the layers were separated. The organic layer was washed with a saturated sodium chloride solution, dried over magnesium sulfate, and concentrated in vacuo. Recrystallization from ethyl acetate provided 680 mg of the desired subtitle intermediate, m.p. >215° C. IR, MS, NMR.

Analysis for $C_{20}H_{18}O_7$: Calc.: C, 64.86; H, 4.90; Found: C, 66.13; H, 5.27.

C. Preparation of 7-methoxycarbonyl-6-{[6-(4-methoxyphenyl)-5-hexenyl]oxy}-9-oxo-9H-xanthene-4-propanoic acid ethyl ester A solution of 361 mg of 6-(4-methoxyphenyl)-5-hexenyl alcohol was dissolved in 20 ml of diethyl ether. Also added were 0.42 ml of triethylamine followed by 0.23 ml of methanesulfonyl chloride After stirring for 1 hour, water was added, the layers were separated, and the organic layer dried and concentrated in vacuo. A small volume of methyl ethyl ketone was added to the residue and this solution was added to a suspension of 2 g of potassium carbonate and the 680 mg of phenol intermediate from Example 6B above in methyl ethyl ketone. The mixture was heated at reflux overnight and then cooled to room temperature. Water was added, the layers were separated, and the organic layer dried and concentrated in vacuo. The resulting oil was purified by high pressure liquid chromatography eluding with a 40–60% ethyl acetate in hexane gradient. The appropriate fractions were combined and concentrated in vacuo. The resulting white solid was crystallized subtitle intermediate, m.p. 107°–109° C.

Analysis for $C_{33}H_{34}O_8$: Calc.: C, 70.83; H, 6.30; Found: C, 71.04; H, 6.13.

D. Preparation of 7-carboxy-3-{[6-(4-methoxyphenyl)-5-hexenyl]oxy}-9-oxo-9H-xanthene-4-propanoic acid The title product was prepared from 240 mg of the diester of Example 6C according to the procedure 1L providing 160 mg of the desired product, m.p. >215° C.

Analysis for $C_{30}H_{28}O_8$: Calc.: C, 69.76; H, 5.46; Found: C, 69.99; H, 5.64.

EXAMPLE 7

7-Carboxy-3-{[6-(4-methoxyphenyl)hexyl]oxy}-9-oxo-9H-xanthene-4-propanoic acid

A. Preparation of 7-methoxycarbonyl-3-{[6-(4-methoxyphenyl)hexyl]oxy}-9-oxo-9H-xanthene-4-propanoic acid ethyl ester A solution of 630 mg of 7-methoxycarbonyl-3-{[6-(4-methoxyphenyl)-5-hexenyl]oxy}-9-oxo-9H-xanthene-4-propanic acid ethyl ester in ethyl acetate was hydrogenated in the presence of 10 mg of 5% palladium on carbon. After hydrogen uptake ceased, the solution was filtered, concentrated in vacuo, and the residue crystallized from ethyl acetate/hexane to provide 580 mg of the desired subtitle intermediate, m.p. 108°–109° C.

Analysis for $C_{33}H_{36}O_8$: Calc.: C, 70.70; H, 6.47; Found C, 70.46; H, 6.64.

B. Preparation of 7-carboxy-3-{[6-(4-methoxyphenyl)hexyl]oxy}-9-oxo-9H-xanthene-4-propanoic acid The title product was prepared from 500 mg of the corresponding diester from the procedure of Example 1L to provide 360 mg of the desired title product, m.p. >210° C.

Analysis for $C_{30}H_{30}O_6$: Calc.: C, 69.47; H, 5.84; Found: C, 69.29; H, 5.90.

EXAMPLE 8

7-Carboxy-3-decyloxy-9-oxo-9H-fluorene-2-propanoic acid

A. Preparation of 2-(2,4-dimethoxyphenyl)-4,4-dimethyloxazoline

A solution of 27.4 g of 2,4-dimethoxybenzoyl chloride in 30 ml of methylene chloride was added dropwise to a solution of 26.2 g of 2-amino-2-methyl-1-propanol in methylene chloride at 0° C. The mixture was allowed to warm to room temperature and stirred overnight. The mixture was filtered and the filtrate washed twice with 1N hydrochloric acid, once with water, dried, and concentrated in vacuo. Excess thionyl chloride was added to the oily residue. After stirring one hour the mixture was poured into diethyl ether. The resulting solid was recovered by filtration and washed with diethyl ether. The solid was added to 1N sodium hydroxide and stirred. The aqueous mixture was extracted with ethyl acetate and the organic layer separated, dried, and concentrated in vacuo. Distillation of the resulting yellow oil at 165°–170° C. at 0.02 mm pressure provided 17.8 g of the desired subtitled intermediate.

B. Preparation of 2-(4-bromophenyl)-4,4-oxaloline

Following the same procedure as found in Example 8A above, 26.15 g of 4-bromobenzoyl chloride and 22.8 g of 2-amino-2-methyl-1-propanol were allowed to react to provide 20.67 g of subtitled intermediate as a colorless oil which was used without distillation.

C. Preparation of 2-(4,4-dimethyloxazolin-2-yl)-5-methoxy-4'-(4,4-dimethyloxazolin-2-yl)biphenyl A Grignard reagent was prepared using 5.4 g of the bromo intermediate from Example 8B above and 0.72 g of magnesium metal in tetrahydrofuran. This Grignard reagent, in turn, was added to a solution of 2 grams of the dimethoxy intermediate from Example 8A above in tetrahydrofuran. The reaction mixture was stirred overnight, then poured into cold aqueous ammonium chloride solution. The mixture was extracted three times with diethyl ether. The organic layers were combined, dried, and concentrated in vacuo. The residue was purified by high pressure liquid chromotography over silica gel eluting with a 20–70% ethyl acetate in hexane gradient. The appropriate fractions were combined and concentrated in vacuo to provide a pale orange oil which crystallized on standing. Recrystallization from hexane provided 2.6 g of the desired subtitled intermediate as a colorless solid. NMR.

D. Preparation of 2,4'-dicarboxy-5-methoxybiphenyl

Two and one half grams of the dioxazoline from Example 8C above were heated at reflux overnight in 4.5N hydrochloric acid. The solution was cooled and treated with sodium hydroxide solution and the resulting oil extracted into ethyl acetate. The organic layer was washed with water, dried, and concentrated in vacuo providing 1.63 g of the desired subtitle intermediate. NMR.

E. Preparation of 2-carboxy-6-methoxy-9-oxo-9H-fluorene

A mixture of 2.5 g of phosphorous pentoxide and 25 ml of methanesulfonic acid were stirred together under a nitrogen atmosphere overnight. To this mixture were added 2.3 g of 2,4'-dicarboxy-5-methoxybiphenyl. The reaction mixture was stirred at room temperature for six hours with the addition of methanesulfonic acid to keep the mixture sufficient for stirring. The mixture was then warmed to 40° C. for one hour, cooled, and poured into ice water. The resulting yellow-green precipitate was recovered by filteration, washed with water, and dried to provide 1.6 g of the desired subtitle intermediate.

F. Preparation of 2-ethoxycarbonyl-6-hydroxy-9-oxo-9H-fluorene

The 1.6 g of methoxy intermediate from Example 8E above were suspended in a mixture of 20 ml of 48% hydrobromic acid and 40 ml of acetic acid. The mixture was heated at reflux for 2 days, cooled, and poured over ice. The resulting solid was recovered by filteration and the mixture added to ethanol. Sulfuric acid was added and the mixture heated at reflux. After three days the mixture was cooled and an equal volume of water was added. The mixture was extracted with ethyl acetate. The combined organic extracts were washed with water, dried, and concentrated in vacuo. The residue was taken up in ethyl acetate, 5 grams of silicon dioxide were added, and the mixture concentrated in vacuo. The loaded silicon dioxide was applied to a silica column and eluted with 50% ethyl acetate in hexane. Appropriate fractions were combined and concentrated in vacuo. NMR indicated the desired subtitled product and approximately 20% of the methoxy ester. The yield was 1.3 g.

G. Preparation of 2-ethoxycarbonyl-6-allyloxy-9-oxo-9H-fluorene

The 1.3 g of phenol from Example 8F above were dissolved in 25 ml of dimethylformamide. To the solution were added 210 mg of 60% sodium hydride in oil. After stirring for one hour, 0.46 ml of allyl bromide were added. The mixture was warmed to 60° C. After one hour, the reaction mixture was cooled and poured into a mixture of ice and 1N hydrochloric acid. The resulting bright yellow precipitate was recovered by filteration, washed with water, and dried to provide 1.58 g of the title product which had a small amount of the methoxy contaminant from the previous reaction as determined by NMR. This material was taken directly to the following step.

H. Preparation of 2-allyl-3-hydroxy-7-ethoxy-carbonyl-9-oxo-9H-fluorene

The 1.57 g of material from Example 8G above were dissolved in 25 ml of diethylaniline and heated at 200°–210° C. for 12 hours. After cooling, ethyl acetate was added to the mixture. The organic solution was washed with dilute hydrochloric acid and concentrated in vacuo. The residue was purified by high pressure liquid chromotography over silica gel using a 15–40% ethyl acetate in hexane gradient. The appropriate fractions were combined and identified as being the pure title product.

I. Preparation of 2-allyl-3-decyloxy-7-ethoxycarbonyl-9-oxo-9H-fluorene

To 280 mg of the phenol from Example 8H above in 25 ml of dimethylformamide were added 40 mg of 60% sodium hydride in oil. After stirring 30 minutes at room temperature, decyl iodide (0.21 ml) was added. The reaction mixture was warmed to 60° C. and stirred overnight, then cooled and poured onto ice. Water and ethyl acetate were added and the layers separated. The organic layer was washed twice with water, dried over magnesium sulfate, filtered, and concentrated in vacuo providing a yellow oil which slowly solidified on standing. The yield was 348 mg. NMR.

J. Preparation of 2-(3-hydroxypropyl)-3-decyloxy-7-ethoxycarbonyl-9-oxo-9H-fluorene To 100 mg of the allyl intermediate from Example 8I above in 15 ml of tetrahydrofuran under a nitrogen atmosphere were added 0.93 ml of a 0.5M solution of 9-borabicyclo[3.3.1]nonane in tetrahydrofuran. After stirring overnight, 3.8 ml of a 3M solution of sodium acetate were added. After stirring vigorously, 0.72 ml of a 30% hydrogen peroxide solution were added. After stirring for 3 hours, the layers were separated. The organic layer was washed with water, dried over magnesium sulfate, filtered, and concentrated in vacuo providing an oily residue. Preparative thin layer chromatography eluting with 30% ethyl acetate in hexane was used to purify the residue. Isolation of the appropriate band provided 62 mg of the title intermediate. NMR.

K. Preparation of 7-ethoxycarbonyl-3-decyloxy-9-oxo-9H-fluorene-2-proponoic acid A solution of 170 mg of 2-(3-hydroxypropyl)-3-decyloxy-7-ethoxycarbonyl-9-oxo-9H-fluorene in diethyl ether were treated with 0.75 ml of Jones reagent (chromic acid solution). The reaction mixture was stirred overnight, poured into water and the layer separated. The organic layer was washed with water, dried over magnesium sulfate, filtered, and concentrated in vacuo providing 90 mg of material which was taken directly to hydrolysis. NMR.

L. Preparation of 7-carboxy-3-decyloxy-9-oxo-9H-fluorene-2-propanoic acid

The 90 mg of material from Example 8K above were dissolved 2 ml of methanol and a couple drops of water. To the solution were added 22.4 mg of potassium hydroxide. After stirring for 4 hours, the solvent was removed by evaporation and water was added to the resulting solid. The aqueous layer was washed with ethyl acetate and then treated with concentrated hydrochloric acid to a pH of approximately 1. The resulting yellow solid was recovered by filtration. Recrystallization from ethyl acetate provided 51 mg of the desired title product m.p. 218°-220° C.

Analysis for $C_{27}H_{32}O_6$:
Calc.: C, 71.66; H, 7.13;
Found: C, 73.19; H, 6.99.

The compounds of Formula I should be useful in treating any condition, including clinical conditions, which is characterized by the excessive release of leukotriene $B_4$. These conditions include immediate type hypersensitivity reactions such as asthma.

The term "excessive release" of leukotriene $B_4$ refers to an amount of the leukotriene sufficient to cause the particular condition associated with such amount. The amount of leukotriene which is considered to be excessive will depend on a variety of factors, including the amount of leukotriene required to cause the particular condition, and the species of the mammal involved. As will be appreciated by those skilled in the art, the success of treating a mammal suffering from or susceptible to a condition characterized by an excessive release of leukotriene with a compound of Formula I will be measured by the regression or prevention of the symptoms of the condition.

Inhibition of Binding of $^3H$-LTB$_4$ to Peripheral Human Neutrophils

The effectiveness of compounds to inhibit the binding of leukotriene $B_4$ to a specific receptor on the membrane of human neutrophils was measured by using an adaptation of a radio-ligand binding assay developed by Goldman and Goetzl, *J. Immunol.*, 129, 1600 (1982). Other investigators have developed similar assays (see, e.g., Kreisle, et al., *J. Exp. Med.*, 157, 628 (1983) and Lin, et al., *Prostaglandins*, 28, 837 (1984)).

Cells used in the assay were isolated by standard techniques of centrifugation on Ficoll-Hypaque, dextran 70 sedimentation and hypotonic lysis. The following procedure was used. Freshly-prepared buffy coat layers from two individuals were obtained from a local blood donor center. The cells were mixed and diluted to 484 ml with phosphate buffered saline containing heparin (10 units/ml) and heat-inactivated calf serum (5%). This was divided into 20 ml aliquots and the aliquots layered on top of Ficoll-Paque (12 ml). The material was then centrifuged at 500 g for 40 minutes at room temperature. The resulting upper layer of platelets and mononuclear cells was discarded. The lower layer containing erythrocytes and neutrophils was retained. Buffer was added (1 ml per 4 ml of lower layer) and the suspension mixed. For each milliliter of this mixture, 0.33 ml of 6% Macrodex was added. After stirring, the cells were allowed to sediment for 1 hour at 37° C. The resulting erythrocyte pellet was discarded and the neutrophil enriched supernatant fluid centrifuged at 500 g for 10 minutes at 4° C. Erythrocytes still present in this cell pellet were lysed by incubating the cells with 5-8 ml ice-cold distilled water for 30-45 seconds. Subsequently, the volume was made up to 50 ml by addition of ice-cold buffer and the cells resuspended. The suspension was then centrifuged at 300 g for 10 minutes at 4° C. The cells were finally resuspended at a cell density of $2 \times 10^7$ cells/ml in the assay buffer. This buffer consisted of Hanks' balanced salt solution and 0.1% ovalbumin (pH 7.3). This isolation procedure resulted in cell preparations of $\geq 90\%$ neutrophils and $\geq 90\%$ viability.

The radio-ligand binding assay was conducted by incubating neutrophils ($1 \times 10^7$ cells) with 0.1-0.2 nM $^3H$-LTB$_4$ (sp. act. 150-220 Curies/mmol) and test compound ($1 \times 10^{-5}M$ and $1 \times 10^{-6}M$) for 10 minutes at 4° C. The amount of bound $^3H$-LTB$_4$ was then measured and compared with the amount bound in the absence of test compound. The assay was carried out in microcentrifuge tubes by adding first 10 $\mu l$ test compound dissolved in DMSO, followed by adding 20 $\mu l$ $^3H$-LTB$_4$ diluted in assay buffer, and finally adding 500 $\mu l$ of the cell suspension. At the end of the 10 minutes incubation, 300 $\mu l$ of a mixture of dibutyl and dinonyl phthalate (7:2) were added and the tubes centrifuged for 2 minutes in a microcentrifuge. The radioactivity bound to the cell pellet was measured by scintillation spectroscopy. Appropriate corrections for nonspecific bonding of $^3H$-LTB$_4$ were made. The results are reported in Table III.

TABLE III

| | LTB$_4$ Binding Inhibition | | |
|---|---|---|---|
| | Drug Concentration* | | |
| Example No. | $10^{-5}M$ | $10^{-6}M$ | $10^{-7}M$ |
| 1 | — | 25 | 2 |
| 2 | — | 27 | −7 |
| 3 | — | 23 | −4 |
| 4 | 102 | 86 | 52 |
| 6 | 102 | 99 | 91 |
| 7 | 106 | 103 | 85 |
| 8 | 68 | 19 | −4 |

*percent inhibition

The compounds or formulations of the present invention may be administered by the oral and rectal routes, topically, parenterally, e.g., by injection and by continuous or discontinuous intra-arterial infusion, in the form of, for example, tablets, lozenges, sublingual tablets, sachets, cachets, elixirs, gels, suspensions, aerosols, ointments, for example, containing from 1 to 10% by weight of the active compound in a suitable base, soft and hard gelatin capsules, suppositories, injectable solutions and suspensions in physiologically acceptable media, and sterile packaged powders adsorbed onto a support material for making injectable solutions. Advantageously for this purpose, compositions may be provided in dosage unit form, preferably each dosage unit containing from about 5 to about 500 mg (from about 5 to 50 mg in the case of parenteral or inhalation administration, and from about 25 to 500 mg in the case of oral or rectal administration) of a compound of Formula I. Dosages from about 0.5 to about 300 mg/kg per day, preferably 0.5 to 20 mg/kg, of active ingredient may be administered although it will, of course, readily be understood that the amount of the compound or compounds of Formula I actually to be administered will be determined by a physician, in the light of all the relevant circumstances including the condition to be treated, the choice of compound to be administered and the choice of route of administration and therefore the above preferred dosage range is not intended to limit the scope of the present invention in any way.

The formulations of the present invention normally will consist of at least one compound of Formula I mixed with a carrier, or diluted by a carrier, or enclosed or encapsulated by an ingestible carrier in the form of a capsule, sachet, cachet, paper or other container or by a disposable container such as an ampoule. A carrier or diluent may be a solid, semisolid or liquid material which serves as a vehicle, excipient or medium for the active therapeutic substance.

Some examples of the diluents or carrier which may be employed in the pharmaceutical compositions of the present invention are lactose, dextrose, sucrose, sorbitol, mannitol, propylene glycol, liquid paraffin, white soft paraffin, kaolin, fumed silicon dioxide, microcrystalline cellulose, calcium silicate, silica, polyvinylpyrrolidone, cetostearyl alcohol, starch, modified starches, gum acacia, calcium phosphate, cocoa butter, ethoxylated esters, oil of theobroma, arachis oil, alginates, tragacanth, gelatin, syrup, methyl cellulose, polyoxyethylene sorbitan monolaurate, ethyl lactate, methyl and propyl hydroxybenzoate, sorbitan trioleate, sorbitan sesquioleate and oleyl alcohol and propellants such as trichloromonofluoromethane, dichlorodifluoromethane and dichlorotetrafluoroethane. In the case of tablets, a lubricant may be incorporated to prevent sticking and binding of the powdered ingredients in the dies and on the punch of the tableting machine. For such purpose there may be employed for instance aluminum, magnesium or calcium stearates, talc or mineral oil.

Preferred pharmaceutical forms of the present invention are capsules, tablets, suppositories, injectable solutions, creams and ointments. Especially preferred are formulations for inhalation application, such as an aerosol, and for oral ingestion.

The following formulation examples may employ as active compounds any of the compounds of this invention. The examples are illustrative only and are not intended to limit the scope of the invention in any way.

EXAMPLE 9

Hard gelatin capsules are prepared using the following ingredients:

| | Quantity (mg/capsule) |
|---|---|
| 7-carboxy-3-{[6-(4-methoxyphenyl)-5-hexenyl]oxy}-9-oxo-9H-xanthene-2-propanoic acid | 250 |
| Starch | 200 |
| Magnesium stearate | 10 |

The above ingredients are mixed and filled into hard gelatin capsules in 460 mg quantities.

EXAMPLE 10

A tablet is prepared using the ingredients below:

| | Quantity (mg/tablet) |
|---|---|
| 7-carboxy-3-{[6-(4-methoxyphenyl)-5-hexenyl]oxy}-9-oxo-9H-fluorene-2-propanoic acid | 250 |
| Cellulose, microcrystalline | 400 |
| Silicon dioxide, fumed | 10 |
| Magnesium stearate | 5 |

The components are blended and compressed to form tablets each weighing 665 mg.

EXAMPLE 11

An aerosol solution is prepared containing the following components:

| | Weight % |
|---|---|
| 7-carboxy-3-{[6-(4-methylthiophenyl)-hexyl]oxy}-9-oxo-9H-fluorene-2-propanoic acid | 0.25 |
| Ethanol | 30.00 |
| Propellant 11 (trichlorofluoromethane) | 10.25 |
| Propellant 12 (Dichlorodifluoromethane) | 29.75 |
| Propellant 114 (Dichlorotetrafluoroethane) | 29.75 |

The active compound is dissolved in the ethanol and the solution is added to the propellant 11, cooled to $-30°$ C. and transferred to a filling device. The required amount is then fed to a container and further filled with the pre-mixed propellants 12 and 114 by means of the cold-filled method or pressure-filled method. The valve units are then fitted to the container.

EXAMPLE 12

Tablets each containing 60 mg of active ingredient are made up as follows:

| | |
|---|---|
| 7-carboxy-3-{[6-(4-methylsulfinylphenyl)-hexyl]oxy}-9-oxo-9H-xanthene-2-propanoic acid | 60 mg |
| Starch | 45 mg |
| Microcrystalline cellulose | 35 mg |
| Polyvinylpyrrolidone (as 10% solution in water) | 4 mg |
| Sodium carboxymethyl starch | 4.5 mg |
| Magnesium stearate | 0.5 mg |
| Talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50°–60° and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

EXAMPLE 13

Capsules each containing 80 mg of medicament are made as follows:

| | |
|---|---|
| 7-Carboxy-3-(decyloxy)-9-oxo-9H-xanthene-4-propanoic acid | 80 mg |
| Starch | 59 mg |
| Microcrystalline cellulose | 59 mg |
| Magnesium stearate | 2 mg |
| Total | 200 mg |

The active ingredient, cellulose, starch and magnesium stearate are blended, passed through a No. 45 mesh U.S. sieve, and filled into hard gelatin capsules in 200 mg quantities.

EXAMPLE 14

Suppositories each containing 225 mg of active ingredient are made as follows:

| | |
|---|---|
| 7-Carboxy-3-{[6-(4-methoxyphenyl)-5-hexenyl]oxy}-9-oxo-9H-xanthene-4-propanoic acid | 225 mg |
| Unsaturated or saturated fatty acid glycerides to | 2,000 mg |

The active ingredient is passed through a No. 60 mesh U.S. sieve and suspended in the fatty acid glycerides previously melted using the minimum heat necessary. The mixture is then poured into a suppository mold of nominal 2 g capacity and allowed to cool.

EXAMPLE 15

Suspensions each containing 50 mg of medicament per 5 ml dose are made as follows:

| | |
|---|---|
| 7-Carboxy-3-{[6-(4-methoxyphenyl)hexyl]oxy}-9-oxo-9H-xanthene-4-propanoic acid | 50 mg |
| Sodium carboxymethyl cellulose | 50 mg |
| Sugar | 1 g |
| Methyl paraben | 0.05 mg |
| Propyl paraben | 0.03 mg |
| Flavor | q.v. |
| Color | q.v. |
| Purified water to | 5 ml |

The medicament is passed through a No. 45 mesh U.S. sieve and mixed with the sodium carboxymethylcellulose, sugar, and a portion of the water to form a suspension. The parabens, flavor and color are dissolved and diluted with some of the water and added, with stirring. Sufficient water is then added to produce the required volume.

I claim:

1. A compound of the Formula I

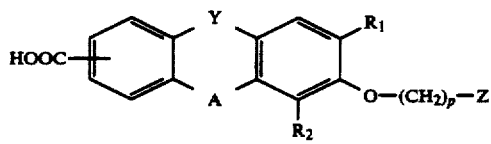

or a pharmaceutically acceptable base addition salt thereof, wherein

Y is —CO—, —C(=NOH)—, —CHOH—, —CH$_2$—, or —C(=CH$_2$)—;

A is —O—;

one of R$_1$ and R$_2$ is hydrogen and the other of R$_1$ and R$_2$ is —CH$_2$CH$_2$COOH;

p is 1–16; and

Z is —H or —G—Q where

G is a bond, —O—, —S(O)$_t$—, —NH—, —CH=CH—, or —C≡C—,

Q is phenyl or phenyl substituted with one or two substituents selected from the group consisting of halo, C$_1$–C$_3$ alkyl, C$_1$–C$_3$ alkoxy, acetyl, nitro, amino, trifluoromethyl, hydroxy, and —S(O)$_t$—(C$_1$–C$_3$ alkyl), and each t is independently 0–2.

2. A compound of claim 1 of the Formula Ia

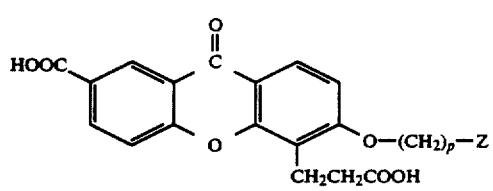

or a pharmaceutically acceptable base addition salt thereof wherein p' is 4–12.

3. The compound of claim 2 which is 7-carboxy-3-(decyloxy)-9-oxo-9H-xanthene-4-propanoic acid or a pharmaceutically acceptable base addition salt thereof.

4. The compound of claim 2 which is 7-carboxy-3-{[6-(4-methoxyphenyl)-5-hexenyl]oxy}-9-oxo-9H-xanthene-4-propanoic acid or a pharmaceutically acceptable base addition salt thereof.

5. The compound of claim 2 which is 7-carboxy-3-{[6-(4-methoxyphenyl)hexyl]oxy}-9-oxo-9H-xanthene-4-propanoic acid or a pharmaceutically acceptable base addition salt thereof.

6. A method of treating a mammal suffering from or susceptible to any condition characterized by an excessive release of leukotrienes, which comprises administering to said mammal a leukotriene antagonizing amount of a compound of claim 1 or a pharmaceutically acceptable base addition salt thereof.

7. A method of treating a mammal suffering from or susceptible to any condition characterized by an excessive release of leukotrienes, which comprises administering to said mammal a leukotriene antagonizing amount of a compound of claim 2.

8. A method of treating a mammal suffering from or susceptible to an immediate hypersensitivity reaction of the type represented by asthma, which comprises administering to said mammal a therapeutically-effective amount of a compound of claim 1 or a pharmaceutically acceptable base addition salt thereof.

9. A method of treating a mammal suffering from or susceptible to an immediate hypersensitivity reaction of the type represented by asthma, which comprises administering to said mammal a therapeutically-effective amount of a compound of claim 2.

10. A pharmaceutical formulation comprising a compound of claim 1 or a pharmaceutically acceptable base addition salt thereof in association with a pharmaceutically acceptable carrier.

11. A pharmaceutical formulation comprising a compound of claim 2 in association with a pharmaceutically acceptable carrier.

12. A formulation according to claim 11 employing 7-carboxy-3-(decyloxy)-9-oxo-9H-xanthene-4-propanoic acid or a pharmaceutically acceptable base addition salt thereof.

13. A formulation according to claim 11 employing 7-carboxy-3-{[6-(4-methoxphenyl)-5-hexenyl]oxy}-9-oxo-9H-xanthene-4-propanoic acid or a pharmaceutically acceptable base addition salt thereof.

14. A formulation according to claim 11 employing 7-carboxy-3-{[6-(4-methoxyphenyl)hexyl]oxy}-9-oxo-9H-xanthene-4-propanoic acid or a pharmaceutically acceptable base addition salt thereof.

* * * * *